United States Patent [19]
Patnode et al.

[11] Patent Number: 5,123,535
[45] Date of Patent: Jun. 23, 1992

[54] STERILE HOLDER FOR X-RAY CASSETTES

[75] Inventors: Gregg A. Patnode; Robert L. Wheeler, both of St. Paul, Minn.

[73] Assignee: Minnesota Mining and Manufacturing Company, St. Paul, Minn.

[21] Appl. No.: 645,559

[22] Filed: Jan. 24, 1991

[51] Int. Cl.⁵ ............................................. B65D 33/20
[52] U.S. Cl. .................... 206/438; 206/455; 383/6; 383/7; 383/93; 383/95
[58] Field of Search ............ 383/93, 94, 95, 87, 383/6, 7, 22; 206/455, 438

[56] References Cited

U.S. PATENT DOCUMENTS

| | | | |
|---|---|---|---|
| 2,754,865 | 7/1956 | Moore | 383/94 |
| 2,819,010 | 1/1958 | Amiguet | 383/93 |
| 2,873,905 | 2/1959 | Denton | 383/22 |
| 3,073,507 | 1/1963 | Trewella | |
| 3,143,278 | 8/1964 | Hiebert | 383/93 |
| 3,510,052 | 5/1970 | Ruda | 383/87 |
| 3,646,726 | 3/1972 | Hutcheson | 383/94 |
| 3,738,566 | 6/1973 | Foster | 383/94 |
| 3,829,699 | 8/1974 | Anspack, Jr. | |
| 3,843,041 | 10/1974 | Oliverius | |
| 3,917,160 | 11/1975 | Olerud | |
| 3,941,245 | 3/1976 | Oliverius | |
| 3,988,873 | 11/1976 | Oliverius | |
| 3,990,627 | 11/1976 | Olson | 383/95 |
| 4,057,731 | 11/1977 | Leseff | |
| 4,822,178 | 4/1989 | Taylor | 383/95 |

Primary Examiner—Stephen P. Garbe
Attorney, Agent, or Firm—Gary L. Griswold; Walter N. Kirn; Jennie G. Boeder

[57] ABSTRACT

A flexible sterilized bag which easily unfolds to receive an x-ray cassette and is easily closed using a pressure-sensitive adhesive coating strip located around the bag. The bag is advantageously used in a surgical or operating room environment. The bag is composed of a sterilized bag portion, a cuff formed at the open end of the bag and a pressure-sensitive adhesive coating along the circumference near the open end of the bag. As the cassette is pushed into the bag the adhesive coating strip becomes reoriented so that the adhesive coating on one side of the bag directly faces the remaining adhesive coating on the other side of the bag. The open end of the bag is then sealed by simply pressing the opposing sides of the bag together at the location of the adhesive coating.

19 Claims, 4 Drawing Sheets

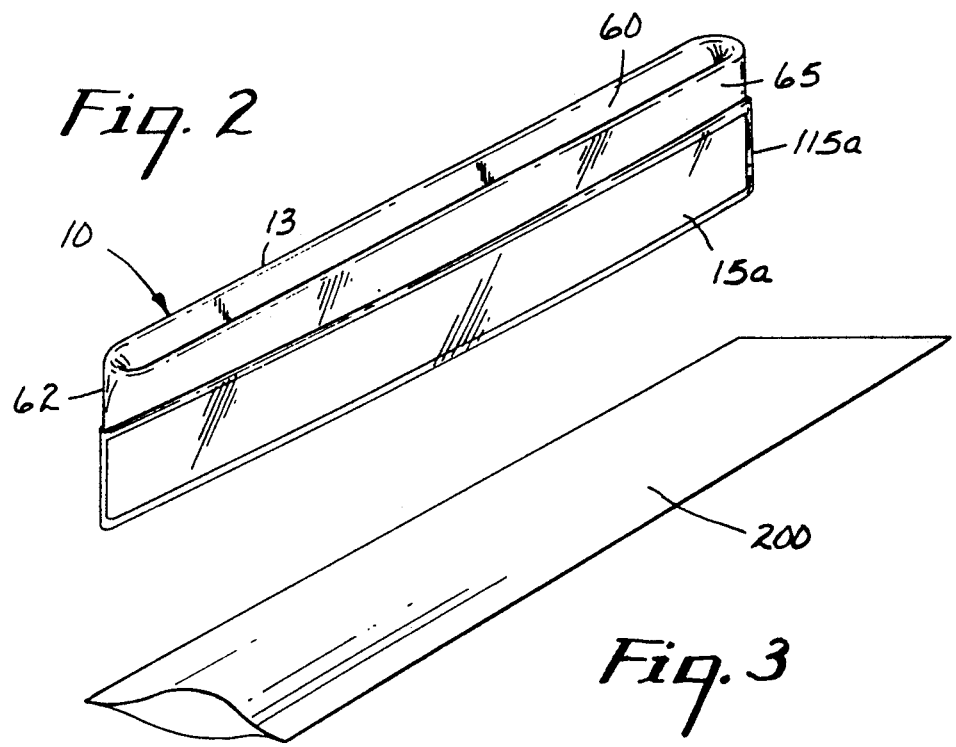
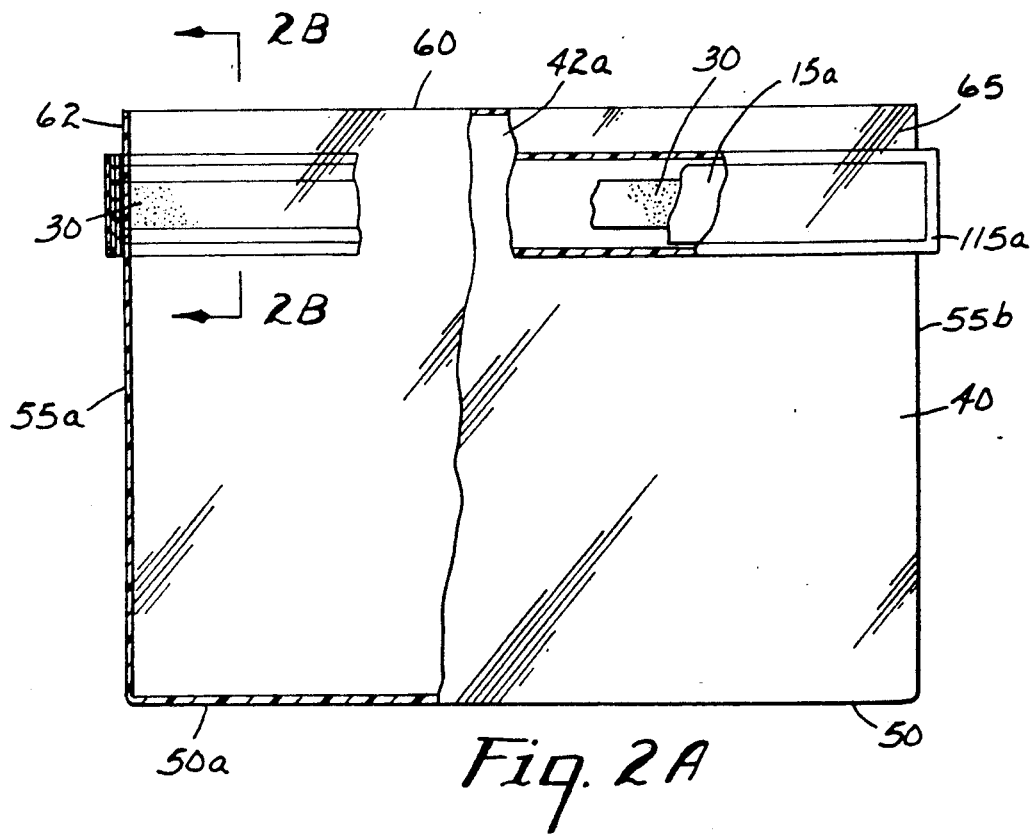

STERILE HOLDER FOR X-RAY CASSETTES

BACKGROUND OF THE INVENTION

1. Field of the Invention

The invention relates to sterile containers for use in a surgical operating room environment. The invention particularly relates to a sterile container for x-ray cassettes.

2. Description of the Prior Art

The prior art discloses various sterile holders for x-ray cassettes. In the surgical or operating room environment, x-ray film contained within a cassette must be placed in contact with or in near proximity to the patient. It is necessary to assure that an open wound does not become contaminated by bacteria on the surface of the x-ray cassette. Since the cassette cannot be sterilized directly, using steam or known chemical sterilants other means must be provided to assure that the cassette does not inadvertently contaminate the patient. Operating room environments have strict requirements of sterility and great precaution must be taken to avoid contamination by any external objects which are brought into the surgical environment.

Various sterile holders are described in the prior art for preventing such x-ray cassettes from contaminating a patient. In U.S. Pat. No. 3,941,245, a sterile container for enclosing non-sterile material such as x-ray cassettes is disclosed. The container disclosed in this reference has the complexity of an outer and inner container. The outer container has a closed end and a cuff adjacent an open end. To enclose non-sterile material in the sterile container a sterile nurse holds the first or outer container while another person moves the non-sterile material into the second or inner container. Related patents belonging to the same family as he foregoing reference are U.S. Pat. Nos. 3,988,873 and 3,843,041.

In U.S. Pat. No. 3,829,699, a sterilized holder for x-ray cassettes is composed of a container having an open flared top. The container includes a cap which has an open bottom with an outwardly extending flare to facilitate entry of the cassette into the container. The cap has a flared end so that it can be placed over the container. The cap also has an indentation around and near its top so it can be snapped over the flared open end of the container. A seal is located around the container to mate with the inner side of the flared portion of the cap. The cap is attached to the container by hinge straps. While the container disclosed in this reference appears to be able to assure operating room sterility once the cassette is placed therein, it has the disadvantage of being composed of a number of components and thereby is costly to manufacture.

In U.S. Pat. No. 3,073,507, a sterilized plastic bag is disclosed which can be readily sterilized after the bag has been packaged and sealed. The flexible bag disclosed in this reference has the advantage that it is of a simple construction and, therefore, readily manufactured. However, the bag is intended to be sterilized after the article has been placed therein. Thus, the flexible bag disclosed in this reference is not suitable for use in a sterile operating room for the intended purpose of preventing contamination by an x-ray cassette, since it would be too cumbersome a procedure to sterilize the bag after the cassette has been placed in the bag.

Accordingly, it is desirable to provide a flexible bag which can be readily manufactured and pre-sterilized and which can be easily used to store x-ray cassettes prior to their use in an operating room environment. It is also desirable to provide efficient and secure sealing of the bag once the x-ray cassette has been placed therein.

SUMMARY OF THE INVENTION

In one aspect of the invention, a flexible sterilized two-sided container is provided which is composed of a sterilized bag portion, a pair of handle strips for holding the bag and a pressure-sensitive adhesive coating or adhesive strip around the circumference near the open end of the bag. The adhesive strip is used to seal the bag after the cassette has been placed therein. The bag itself is closed at one end and open at the other. The open end is folded over onto itself forming a cuff portion. A pair of plastic handle strips are secured to the cuff on each side of the bag. The sterilized bag portion may be folded into and between the area between the pair of handle strips. The handles thus protect the bag from contamination prior to use.

As an x-ray cassette is inserted into the bag the bag portion unfolds from between the two handle strips. The adhesive strip around the bag circumference becomes inverted so that an adhesive seal can be formed as the bag is unfolded from between the handle strips.

In another aspect of the invention a flap is formed on the cuff portion. The flap can be folded to form a sleeve for each of the handle strips. The handle strips are inserted during manufacture within each of the sleeves and are held in place by heat sealing the ends of the sleeve itself. In this aspect of the invention, the bag is folded prior to use so that a portion of the outside of the bag is exposed on the surface of the handle strip rather than being folded between the handle strips. The folded bag can be inserted into a separate protective sleeve prior to use. As an x-ray cassette is pushed or falls into the bag, the cuff disengages from an adhesive strip on the inside surface of the flap. The cuff, as it disengages from the adhesive strip, inverts into the interior of the bag allowing the adhesive strip to be engageable by pressing the bag together at the open end thereof to seal the bag.

An advantage of the present invention is that the bag is readily manufactured. Sterility of the bag is assured. The bag is very easy to use since one need only insert the x-ray cassette into the bag. As the cassette is pushed or falls down into the bag, the bag is pulled downwardly and the adhesive strip near the open end of the bag becomes inverted or is reoriented so that the adhesive portions directly face each other and may be easily pressed into contact to securely and firmly seal the bag.

BRIEF DESCRIPTION OF THE DRAWINGS

FIG. 2 shows another embodiment of the bag in a packaged position prior to use.

FIG. 2A shows the embodiment of FIG. 2 in open, unfolded, position and ready to receive an article.

FIG. 3 is a perspective view of the separate sleeve.

DETAILED DESCRIPTION

Figure 1:
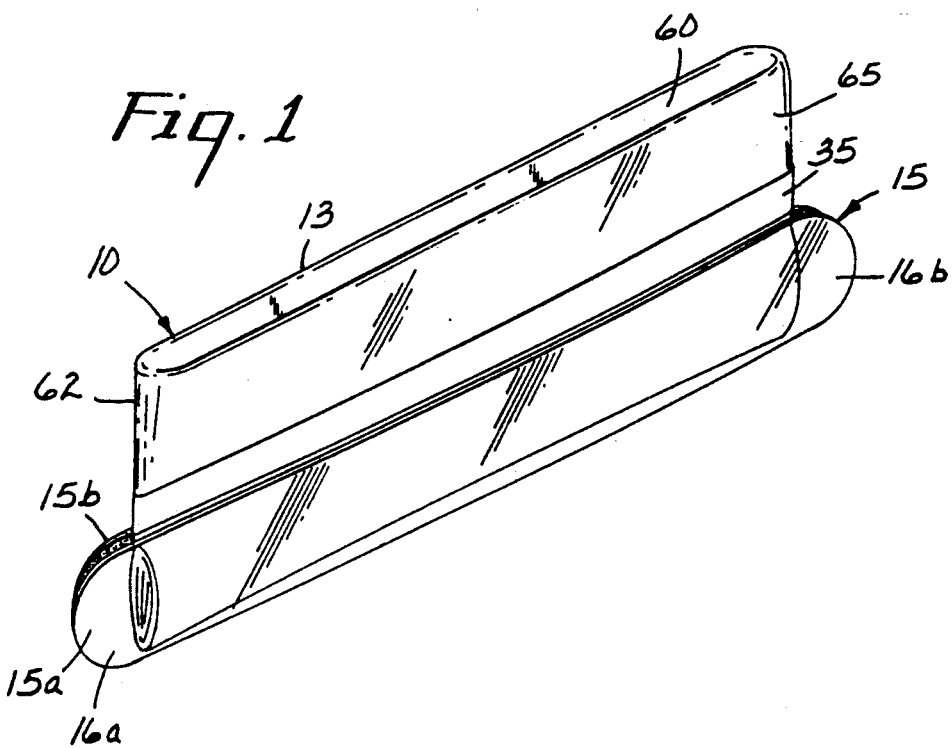
FIG. 1 is an embodiment of the invention showing the bag in closed or packaged position prior to use.
Figure 1A:
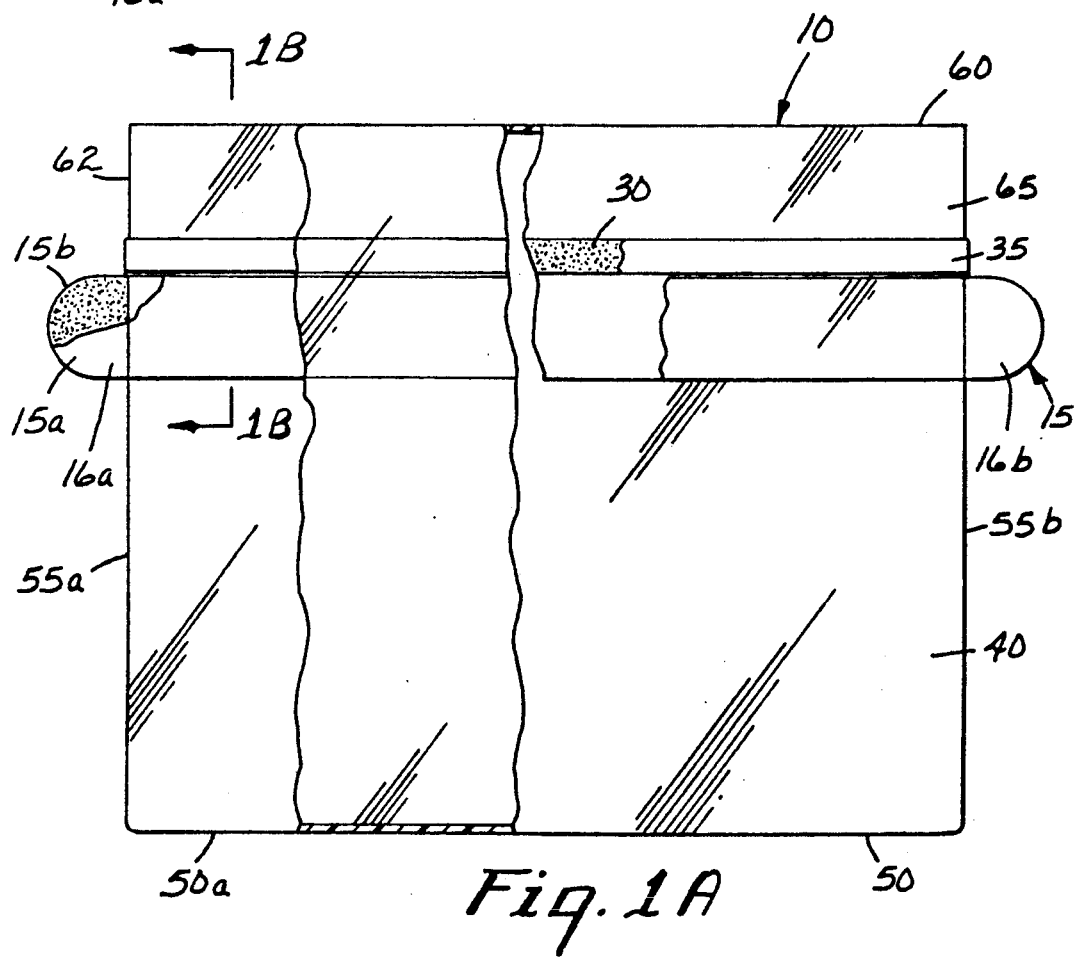
FIG. 1A is an embodiment of the invention as shown in FIG. 1 after the bag is unfolded, open and ready to receive an article, parts thereof cut away.
Figure 1C:
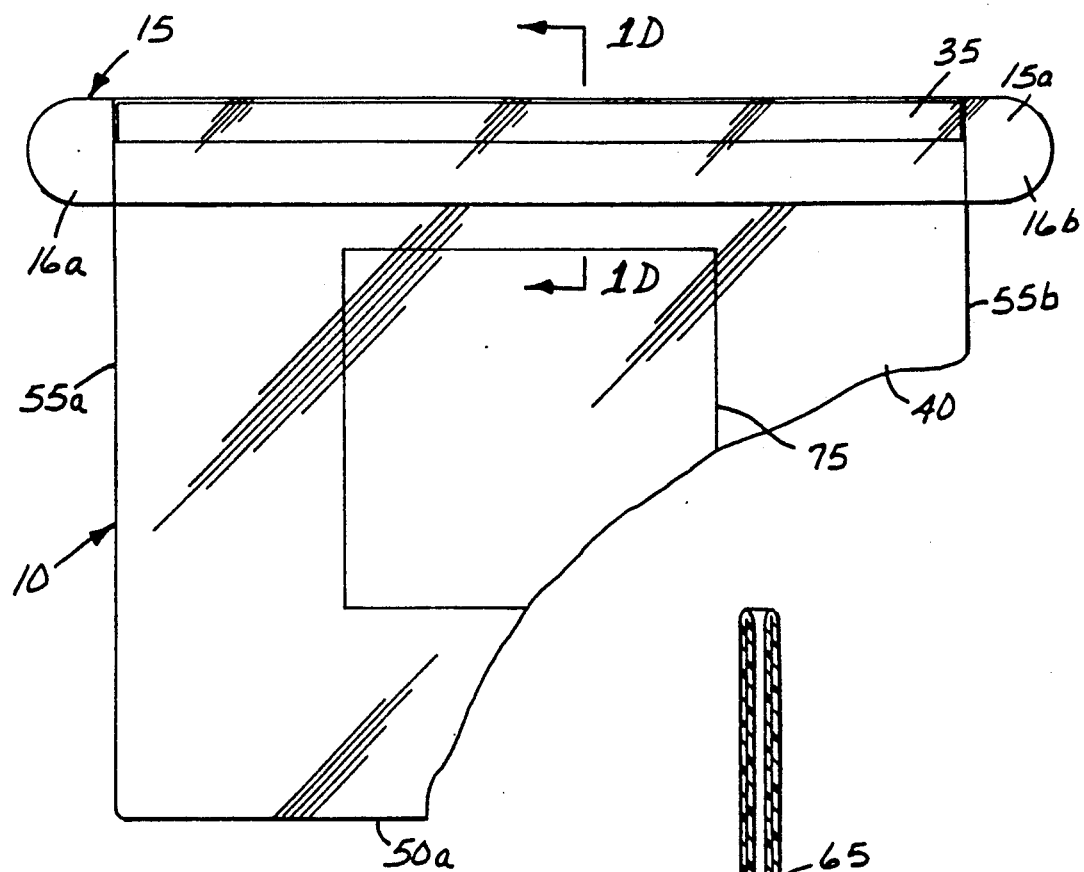
FIG. 1C shows the bag after an article is inserted therein and the cuff portion inverted, parts thereof cut away.
Figure 1D:
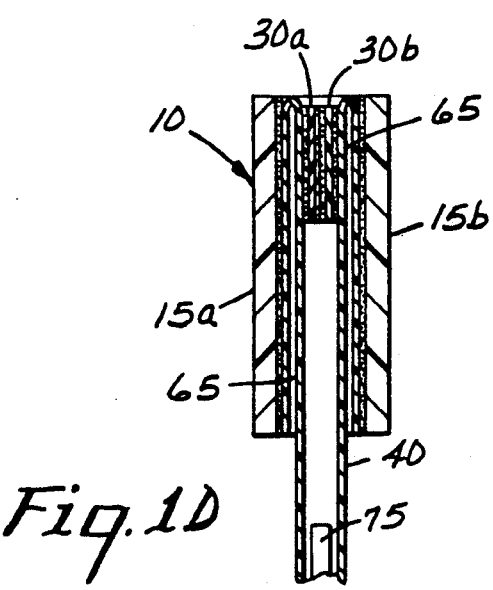
FIG. 1D is a sectional end view of the bag illustrated in FIG. 1C.
Figure 1B:
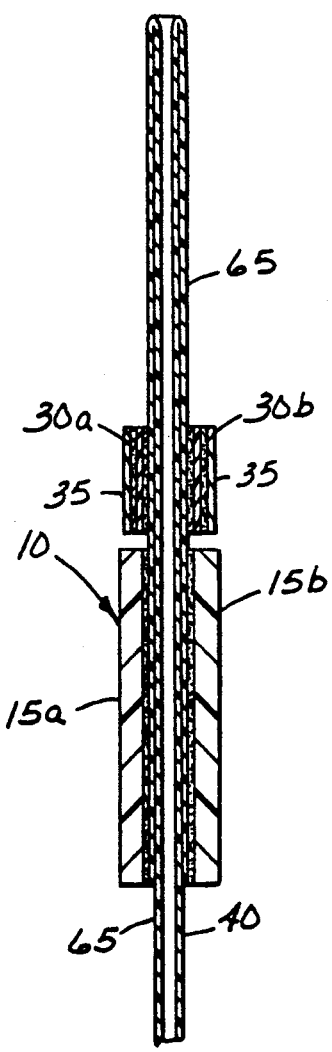
FIG. 1B is a sectional end view of the bag illustrated in FIG. 1A.

Preferred embodiments of the invention are illustrated in the drawings. A first preferred embodiment of the sterilized container of the invention is illustrated in FIGS. 1, 1A, through 1D. The container 10 of the invention, as shown prior to insertion of an x-ray cassette in FIG. 1A, is composed of a bag portion 40, a handling portion such as a pair of handle strips 15a and 15b, and an adhesive strip 30 which runs circumferentially around the bag. The bag is manufactured to have a closed end 50, opposing closed sides 55a and 55b and is open at the remaining or top end 60. The bag portion 40 is preferably formed from one piece of plastic film, preferably polyethylene film, which is folded at fold line 50a and heat sealed along lines 55a and 55b. The top portion 62 adjacent the open end 60 of bag 40 is folded over its exterior surface along fold line 13 to form a cuff 65. Cuff portion 65 may extend several inches, typically 4 or 5 inches down the length of the bag. Cuff 65 contains a handling or gripping portion. The handling portion is preferably a pair of handle strips 15a and 15b, preferably of clear polystyrene, typically having a width of several inches, preferably about 2 to 3 inches (5 to 8 cm). Handle strips 15a and 15b may be adhesively secured to either side of the bag. A strip of pressure-sensitive adhesive 30 is coated or applied by transfer tape around the bag just above the handle strips 15a and 15b. Adhesive strip 30 is protected with conventional release liner 35 which is readily peelable from adhesive 30 just prior to sealing of the bag.

Bag 40 is preferably formed of polyethylene film having a thickness between about 2 and 4 mil, preferably 3 mil. Alternatively, bag 40 may advantageously be composed of polypropylene or other suitable clear plastic film of same thickness. Handle strips 15a and 15b preferably have a thickness of between about 30 to 60 mil. Alternatively, handle strips 15a and 15b may conveniently be formed of polyethylene having a thickness of between about 30 to 60 mil. Adhesive strip 30 may be selected from a wide variety of pressure-sensitive adhesives which are known to form a permanent bond and are easily coated onto polyethylene or polypropylene film. Adhesive strip 30 is advantageously an acrylic pressure-sensitive adhesive such as that available under the trademark "SCOTCH" High Tack/Low Tack Y-9415 Adhesive from 3M Industrial Specialties Division, St. Paul, Minnesota. Alternatively mechanical releasable seals such as those sold under the trademarks "ZI-PLOK" (Dow Chemical Co.), "VELCRO" (Velcro Co.), "SCOTCHMATE" (3M Co.), or equivalent seals could be employed in place of adhesive strip 30 to seal bag 40. Handle strips 15a and 15b, as shown, are secured to the outer surface of the bag 40 preferably at the lower end of cuff portion 65, preferably using an acrylic permanent pressure-sensitive adhesive, for example, as available from 3M Medical Surgical Division, St. Paul, Minnesota, under the trade designation "Transfer Adhesive No. 1522."

During manufacture, after bag 40 has been formed and handle strips 15a and 15b have been secured thereto, the bag itself is sterilized by exposing it to gamma radiation or ethylene oxide vapor. Thereupon, the bag is folded from the bottom up into and between the area bounded by handle strips 15a and 15b. The handle strips 15a and 15b thus protect the sterile quality of the bag. The folded bag may be encased in a separate sterile sleeve or envelope 200 if desired. Handles 15a and 15b are also secured to each other at ends 16a and 16b thereof preferably using acrylic-permanent pressure-sensitive adhesive, for example, "Transfer Adhesive No. 1522," available from 3M Medical Surgical Division. Alternatively handles 15a and 15b may be heat sealed together or else fastened together by use of fasteners or equivalent.

The sterilized container 10 in its prepackage form prior to use is shown in FIG. 1. When it is desired to use the container 10, a non-sterile person may insert the x-ray cassette into the open end 60 of bag portion 40 and let the cassette fall downwardly while a sterile person grips handle strips 15a and 15b and holds bag 40 open. In so doing the bottom portion of the bag will drop downwardly from between handle strips 15a and 15b to form the open bag configuration shown in FIG 1A. As the cassette 75 is pushed or falls into bag 40, top portion 62 of cuff 65 becomes inverted so that its outside surface now becomes part of the inside surface of bag 40 as best illustrated in FIG. 1D. The inversion of cuff 65 allows for the accidental contamination of cuff 65 by cassette 75 while the cassette 75 is being inserted, since the potentially contaminated cuff 65 is sealed inside bag 40 by the inversion process. As top portion 62 becomes inverted adhesive strip 30 surrounding the bag also is inverted so that adhesive strip portion 30a on one side of the bag faces the adhesive strip portion 30b on the opposite side of the bag. Just prior to insertion of x-ray cassette 75, the user removes release liner 35 of adhesive strip 30 so that when top portion 62 becomes inverted exposed adhesive strip layer 30a on one side of the bag faces exposed adhesive strip 30b on the opposite side of the bag. Accordingly, after the inversion of top portion 62 is effected, the user need only press the facing adhesive strip portions 30a and 30b against each other to form a secure pressure-sensitive adhesive seal which effectively closes the top open end 60 of bag 40. The preferred "SCOTCH" brand High Tack/Low Tack Y-9415 adhesive strip 30, however, allows the user to reopen and reclose bag 40 after use, since adhesive 30a and 30b forms a releasable, readhering bond between one another.

Figure 2C:
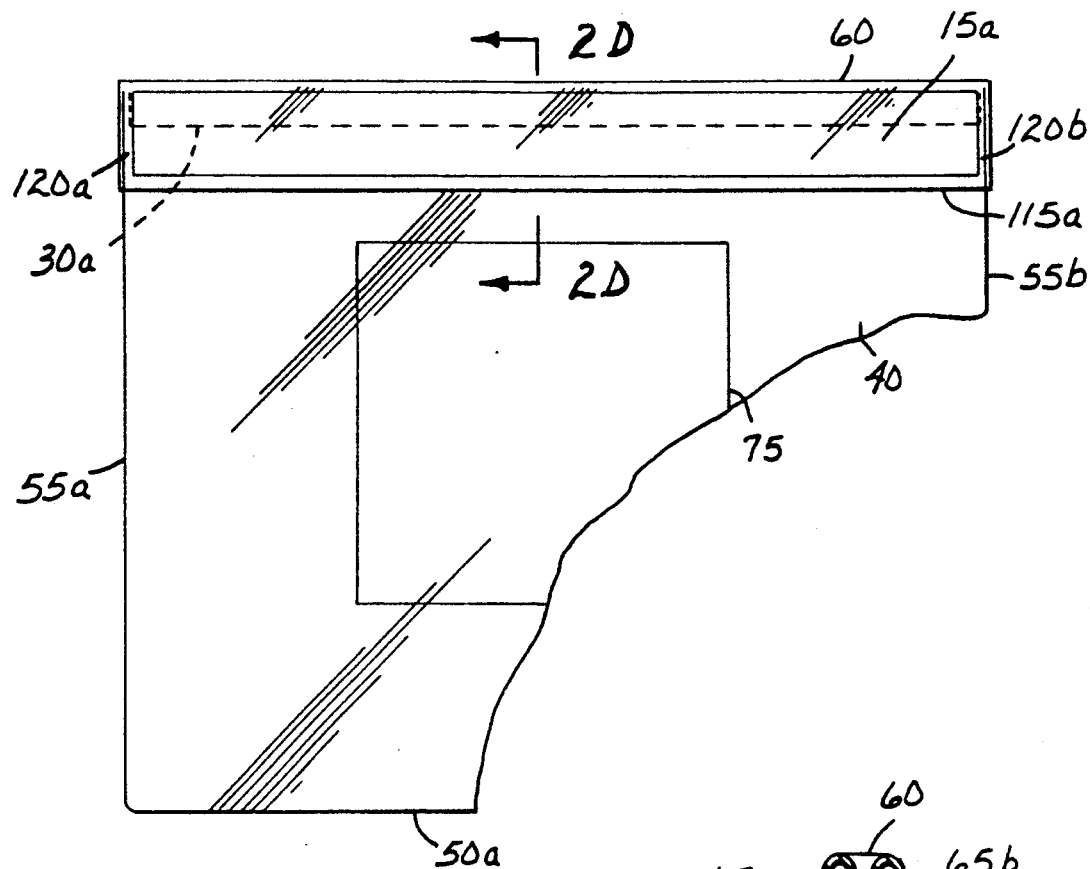
FIG. 2C shows the embodiment of FIG. 2 after an article has been inserted in the bag and the bag is in position to be sealed.
Figure 2D:
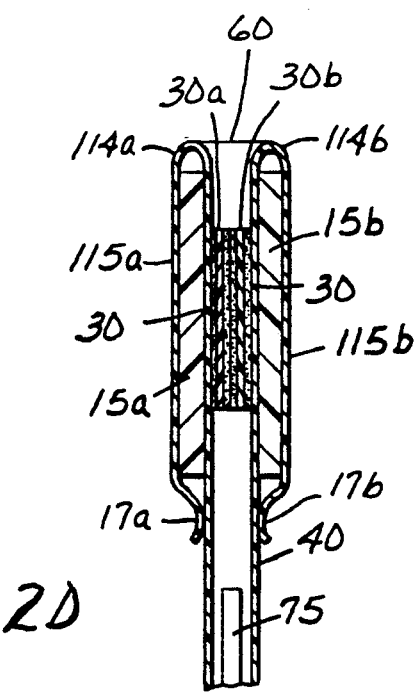
FIG. 2D is a sectional end view of the bag illustrated in FIG. 2C.
Figure 2B:
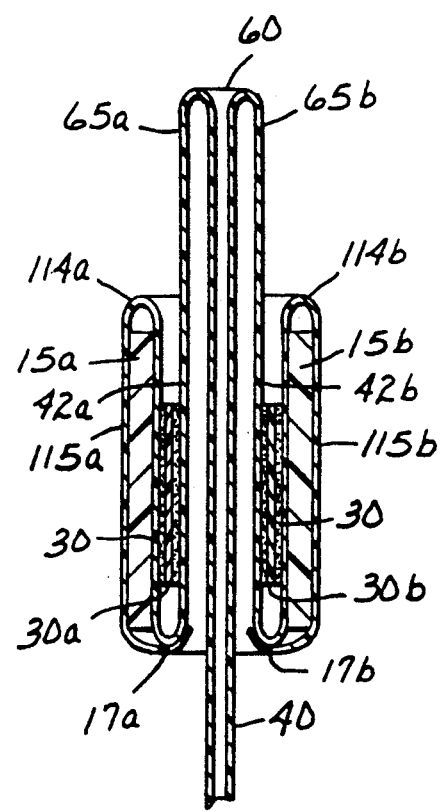
FIG. 2B is a sectional end view of the bag illustrated in FIG. 2A.

An alternate preferred embodiment of the invention is shown in FIGS. 2 through 2D. This embodiment is similar to the embodiment shown and described with respect to the foregoing FIGS. 1, through 1D. The difference between the FIG. 2 embodiment and the FIG. 1 embodiment is that flaps 114a and 114b are formed on the cuff portion 65 by folding a portion of cuff 65 over an exposed portion of said cuff. Flaps 114a and 114b can be made to form sleeve pockets 115a and 115b for handles 15a and 15b, respectively, as illustrated in FIGS. 2 through 2D. Sleeve pockets 115a and 115b can be conveniently made by folding a portion of flaps 114a and 114b, respectively, into a sleeve configuration and sealing the folded portion along edge 17a and 17b, respectively, as shown in FIG. 2B. Once the sleeve pockets 115a and 115b have been formed during manufacture of the bag, handle strips 15a and 15b respectively are inserted into said sleeve pockets. The sleeve pockets 115a and 115b are then heat sealed or taped closed at each end 120a and 120b. Preferably adhesive is not used to secure the handle strip 15a and 15b within their respective sleeve pockets, rather the handle strips 15a and 15b are held in place within sleeve pockets 115a and 115b by friction and the sealed ends 120a and 120b on either end of each of the sleeve pockets. The handle strips 15a and 15b are not glued or secured to one another, but rather are separately housed within each respective sleeve pocket 115a and 115b.

Another difference is that the FIG. 2 embodiment preferably does not include a separate releasable liner for adhesive coating 30. Rather adhesive coating strip 30 can be positioned between the inside surface of flaps 114a and 114b and the inside surface of cuff 65. Adhesive coating strip 30 is preferably located on the outside surface of sleeves 115a and 115b behind respective handle strips 15a and 15b as best illustrated in FIG. 2A. In the embodiments illustrated in FIG. 2B a portion 42a and 42b of cuff 65a and 65b, respectively, of bag 40 comes into contact with adhesive coating strip 30a and 30b, respectively, to protect the adhesive prior to insertion of an x-ray cassette in the bag. Portions 42a and 42b serve as a releasable liner for adhesive coating 30a and 30b, respectively. During manufacture the bag 40 is folded and rests in a folded position on one of the surface of either handle strip 15a or 15b, as best illustrated in FIG. 2. The bag 40 prior to folding was subjected to a sterilization process using either gamma radiation or by exposing the bag to ethylene oxide vapor. After the bag has been folded, as shown in FIG. 2, the sterilized bag is then inserted into a separate sterile plastic envelope 200 (not shown). Alternatively, prior to use, the bag could be sterilized by sterilization equipment existing in a hospital environment. In order to use the bag, the user simply removes bag 40 from the sterile envelope and allows bag 40 simply to unfold by force of gravity. At this point, the x-ray cassette 75 may be inserted into open end 60 by a non-sterile person while a sterile person grips handle portions 15a and 15b and holds bag 40 open. As the x-ray cassette is pushed into the bag, top portion 62 of cuff 65 inverts in the same manner described with reference to the FIGS. 1 through 1D embodiment. The cuff portions 42a and 42b (FIG. 2B) adhering to adhesive strip 30a and 30b, respectively, are pulled down and disengage from said strips so that exposed adhesive 30a on one side of the bag faces exposed adhesive 30b on the other side of the bag. At this time the user simply presses the oppositely facing exposed adhesive strips 30a and 30b together in order to seal bag 40 as shown in FIG. 2D. The x-ray cassette 75 is sealed completely from the environment, and bag 40 and x-ray cassette 75 sealed therein can then be brought into a sterile environment such as a surgical or operating room without risk of contaminating a patient undergoing surgery. The sterile bag 40 can then be placed in contact with an exposed wound in order to take required x-rays without risk that the x-ray cassette 75 therein will contaminate the patient's wound. The bag 40 in this FIG. 2 embodiment can also advantageously be reopened and reclosed if the "SCOTCH" brand High Tack/Low Tack Y-9415 adhesive for adhesive strips 30a and 30b is employed.

Although the container of the invention was described with respect to specific preferred embodiments, it should be appreciated that other embodiments utilizing the concept of the present invention are possible without departing from the scope of the invention. The invention is not intended to be limited to specific materials used for the bag and is also not intended to be limited to specific adhesives described in the disclosure. The container of the invention is not intended to be limited to storing an x-ray cassette, since the container can also be used to store other medical articles. It is not intended, therefore, that the invention be limited to the preferred embodiments described herein but rather the invention is defined by the claims and equivalents thereof.

What is claimed is:

1. A flexible container for receiving and isolating a non-sterile medical article, said container comprising:
   a) a flexible sterile bag having an open end and a closed end, and having an inside surface and an exposed outside surface,
   b) an invertible cuff portion formed by folding a portion of said bag along a fold line at the open end of said bag and formed so that as an article is pushed into the bag the cuff portion inverts into the interior of the bag,
   c) a handling portion of said cuff portion for manually gripping and holding said container,
   d) means for sealing the bag, said means positioned on the exposed outside surface of the cuff portion along the circumference of the cuff and between the fold line and the handling portion, so that as said article is pushed into the bag, the cuff portion and sealing means invert causing said sealing means to face the interior of the bag along the inside surface of the bag, said sealing means then being engageable by pressing the bag together at the open end thereof to seal the bag.

2. A flexible container as in claim 1 wherein the sealing means is a strip of pressure-sensitive adhesive placed circumferentially around the exposed surface of the cuff.

3. A flexible container as in claim 2 wherein said adhesive strip is covered with a removable protective release liner, said liner being removed prior to sealing said bag.

4. A flexible container as in claim 1 wherein the handling portion comprising handles of at least two plastic strips affixed to substantially opposite sides of the bag, said cuff portion terminating in proximity to said handles.

5. A flexible container as in claim 4 wherein said handles are formed of rigid or semi rigid plastic strips at least about one inch wide, said plastic strips inserted in sleeves located on the cuff surface, said sleeves formed of the cuff material and said sleeves being sealed to prevent the plastic strips from disengaging from the bag.

6. A flexible container as in claim 5 wherein the flexible bag is in a folded state with the bag folded into the area between said handles prior to use and said flexible container is in a separate sleeve to preserve the sterile condition of the bag.

7. A flexible container as in claim 4 wherein said handles are formed of rigid or semi rigid plastic strips at least about one inch wide, said plastic strips secured to the outside surface of the cuff by adhesive.

8. A flexible container as in claim 7 wherein the flexible bag is in a folded state with the bag folded between said handles prior to use.

9. A flexible container for receiving a non-sterile medical article, said container comprising:
   a) a flexible sterile bag having an open end and a closed end,
   b) an invertible cuff portion formed by folding a portion of said bag over the exposed sides of the bag at the open end thereof and formed so that as an article is pushed into the bag the cuff portion inverts into the interior of the bag,
   c) a flap formed on said cuff portion by folding a portion of the surface of the cuff over an exposed portion of said cuff, said flap having an outside surface and an inside surface, the inside surface facing said cuff and in contact with said cuff,
   d) a handling portion in contact with said flap for manually gripping and holding said container,
   e) an adhesive strip for sealing the bag, said adhesive strip positioned between the inside surface of the flap and the adjacent surface of the cuff, and as an article is pushed into the bag the cuff inverts into the interior of the bag, said adhesive strip being engageable by pressing the bag together at the open end thereof to seal the bag.

10. A flexible container as in claim 9 wherein the adhesive strip is positioned on the inside surface of the flap permitting the cuff to adhesively engage the flap, and as an article is placed into the bag, the cuff disengages from the flap and inverts into the interior of the bag.

11. A flexible container as in claim 9 wherein the flap forms a sleeve located at a terminal end of said cuff portion.

12. A flexible container as in claim 11 wherein the handling portion comprises a rigid or semirigid plastic strip within said sleeve.

13. A flexible container as in claim 12 wherein the sleeve is closed on all sides to retain the plastic strip therein.

14. A flexible container as in claim 9 wherein the adhesive strip is a releasable and readhering pressure sensitive adhesive strip permitting reopening and reclosing of said bag.

15. A flexible container for receiving and isolating a non-sterile medical article, said container comprising:
   a) a flexible bag having an open end and a closed end, and having an inside surface and an exposed outside surface,
   b) a cuff portion formed by folding a portion of said bag along a fold line at the open end of said bag,
   c) a handling portion on said cuff portion for manually gripping and holding said container, said handling portion formed of rigid or semi rigid plastic strips at least about one inch wide affixed to substantially opposite sides of the bag by inserting said plastic strips in sleeves located on the cuff surface, said sleeves formed of the cuff material and said sleeves being sealed to prevent the plastic strips from disengaging from the bag, said cuff portion terminating in proximity to said handles,
   d) means for sealing the bag, said means positioned on the exposed outside surface of the cuff portion along the circumference of the cuff and between the fold line and the handling portion, so that as the article is pushed into the bag, the cuff portion inverts causing said sealing means to face the interior of the bag along the inside surface of the bag, said sealing means then being engageable by pressing the bag together at the open end thereof to seal the bag.

16. A flexible container for receiving a non-sterile medical article, said container comprising:
   a) a flexible bag having an open end and a closed end,
   b) a cuff portion formed by folding a portion of said bag over the exposed sides of the bag at the open end thereof,
   c) a flap formed on said cuff portion forming a sleeve located at a terminal end of said cuff portion by folding a portion of the surface of the cuff over an exposed portion of said cuff, said flap having an outside surface and an inside surface, the inside surface facing said cuff and in contact with said cuff,
   d) a handling portion for manually gripping and holding said container, said handling portion comprising a rigid or semirigid plastic strip within said sleeve,
   e) an adhesive strip for sealing the bag, said adhesive strip positioned between the inside surface of the flap and the adjacent surface of the cuff, and as an article is pushed into the bag the cuff inverts into the interior of the bag, said adhesive strip being engageable by pressing the bag together at the open end thereof to seal the bag.

17. A flexible container for receiving a non-sterile medical article, said container comprising:
   a) a flexible bag having an open end and a closed end,
   b) an invertible cuff portion formed by folding a portion of said bag over the exposed sides of the bag at the open end thereof, said cuff portion inverting as an article is pushed into the bag,
   c) a flap formed on said cuff portion by folding a portion of the surface of the cuff over an exposed portion of said cuff, said flap having an outside surface and an inside surface, the inside surface facing said cuff and in contact with said cuff,
   d) a handling portion for manually gripping and holding said container,
   e) an adhesive strip for sealing the bag, said adhesive strip positioned between the inside surface of the flap and the adjacent surface of the cuff, so that as an article is pushed into the bag the cuff inverts into the interior of the bag, said adhesive strip being engageable by pressing the bag together at the open end thereof to seal the bag.

18. A flexible container for receiving and isolating an x-ray cassette, said container comprising:
   a) a flexible sterile bag having an open end and a closed end, and having an inside surface and an exposed outside surface,
   b) an invertible cuff portion formed by folding a portion of said bag along a fold line at the open end of said bag and formed so that as the x-ray cassette is pushed into the bag the cuff portion inverts into the interior of the bag,
   c) a handling portion on said cuff portion for manually gripping and holding said container,
   d) means for sealing the bag, said means positioned on the exposed outside surface of the cuff portion along the circumference of the cuff and between the fold line and the handling portion, so that as said x-ray cassette is pushed into the bag, the cuff portion and sealing means invert causing said sealing means to face the interior of the bag along the inside surface of the bag, said sealing means being engageable by pressing the bag together at the open end thereof to seal the bag.

19. A flexible container for receiving an x-ray cassette, said container comprising:
a) a flexible sterile bag having an open end and a closed end,
b) an invertible cuff portion formed by folding a portion of said bag over the exposed sides of the bag at an open end thereof and formed so that as an article is pushed into the bag the cuff portion inverts into the interior of the bag,
c) a flap formed on said cuff portion by folding a portion of the surface of the cuff over an exposed portion of said cuff, said flap having an outside surface and an inside surface, the inside surface facing said cuff and in contact with said cuff,
d) a handling portion for manually gripping and holding said container,
e) an adhesive strip for sealing the bag, said adhesive strip positioned between the inside surface of the flap and the adjacent surface of the cuff, and as an article is pushed into the bag the cuff inverts into the interior of the bag, said adhesive strip being engageable by pressing the bag together at the open end and thereof to seal the bag.

* * * * *

UNITED STATES PATENT AND TRADEMARK OFFICE
CERTIFICATE OF CORRECTION

PATENT NO. : 5,123,535
DATED : June 23, 1992
INVENTOR(S) : Gregg A. Patnode and Robert L. Wheeler It is certified that error appears in the above-indentified patent and that said Letters Patent is hereby corrected as shown below:

Col. 5, line 36, "(not shown)" should be deleted.

Signed and Sealed this

Seventh Day of March, 1995

Attest:

BRUCE LEHMAN

Attesting Officer
Commissioner of Patents and Trademarks